(12) United States Patent
Biffin et al.

(10) Patent No.: US 8,999,962 B2
(45) Date of Patent: Apr. 7, 2015

(54) METHOD FOR INCREASING BONE DENSITY AND/OR REDUCING ANY OSTEOCHONDRAL DEFECTS IN AN ANIMAL AND A COMPOSITION INCLUDING VITAMIN K

(76) Inventors: John Ray Biffin, High Range (AU); Hubertus Leonardus Regtop, Mittagong (AU)

( * ) Notice: Subject to any disclaimer, the term of this patent is extended or adjusted under 35 U.S.C. 154(b) by 392 days.

(21) Appl. No.: 12/995,614

(22) PCT Filed: Jun. 2, 2009

(86) PCT No.: PCT/AU2009/000693
§ 371 (c)(1),
(2), (4) Date: Feb. 8, 2011

(87) PCT Pub. No.: WO2009/146490
PCT Pub. Date: Dec. 10, 2009

(65) Prior Publication Data
US 2011/0124610 A1 May 26, 2011

(30) Foreign Application Priority Data

Jun. 3, 2008 (AU) .............................. 2008902795
Jun. 2, 2009 (WO) ................ PCT/AU2009/000693

(51) Int. Cl.
*A01N 45/00* (2006.01)
*A61K 9/14* (2006.01)
*A23K 1/16* (2006.01)
*A23L 1/302* (2006.01)
*A61K 9/00* (2006.01)
*A61K 31/015* (2006.01)
*A61K 31/122* (2006.01)
*A61K 31/59* (2006.01)
*A61K 31/593* (2006.01)
*A61K 45/06* (2006.01)
*A61K 47/10* (2006.01)
*A61K 47/36* (2006.01)
*A61K 47/40* (2006.01)
*A61K 47/44* (2006.01)

(52) U.S. Cl.
CPC .............. *A61K 9/146* (2013.01); *A23K 1/1603* (2013.01); *A23L 1/302* (2013.01); *A61K 9/0095* (2013.01); *A61K 31/015* (2013.01); *A61K 31/122* (2013.01); *A61K 31/59* (2013.01); *A61K 31/593* (2013.01); *A61K 45/06* (2013.01); *A61K 47/10* (2013.01); *A61K 47/36* (2013.01); *A61K 47/40* (2013.01); *A61K 47/44* (2013.01); *A23V 2002/00* (2013.01)

(58) Field of Classification Search
None
See application file for complete search history.

(56) References Cited

U.S. PATENT DOCUMENTS

| | | |
|---|---|---|
| 5,985,335 A | 11/1999 | Dietl et al. |
| 6,436,446 B1 | 8/2002 | Forusz et al. |
| 6,761,912 B2 | 7/2004 | Forusz et al. |
| 6,854,468 B2 | 2/2005 | Schwartz et al. |
| 6,936,286 B2 | 8/2005 | Gorsek et al. |
| 7,311,919 B2 | 12/2007 | Kadota et al. |
| 7,326,733 B2 | 2/2008 | Stashenko et al. |
| 2003/0045510 A1 | 3/2003 | Schloss |
| 2005/0092969 A1 | 5/2005 | Udea et al. |
| 2005/0123603 A1 | 6/2005 | Dalland et al. |

FOREIGN PATENT DOCUMENTS

| | | | |
|---|---|---|---|
| BE | 1016895 | 9/2007 | |
| GB | 2370503 | 7/2002 | |
| JP | 58-55416 | * 4/1983 | ............ A61K 31/12 |
| JP | 3459932 | 2/1998 | |
| WO | 99/00135 | 1/1999 | |
| WO | 02/47493 | 6/2002 | |
| WO | 02/074308 | 9/2002 | |
| WO | WO 2007/046123 | 4/2007 | |

OTHER PUBLICATIONS

Derwent Accession No. 1983-45391K—English language Summary of JP 58-55416.*
Johnston et al (J Am Vet Med Assoc 194:405-409, 1989; Abstract only).*
Szejtli J., (1988) "Cyclodextrin Technology", Kulwer Academic Publishers, pp. 125 and 270).
Szulc et al., (1996), "Serum undercarboxylated osteocalcin is a marker of the risk of hip fracture: a three year follow-up study." Bone 18:487-488.
Thijssen et al., (2002), "Menaquinone-4 in breast milk is derived from dietary phylloquinone." Br J Nutr. 87(3):219-26.
Tovar et al., (2006), "Extrahepatic tissue concentrations of vitamin K are lower in rats fed a high vitamin E diet." Nutrition and Metabol. 3:29.
Tsugawa et al., (2008), "Low plasma phylloquinone concentration is associated with high incidence of vertebral fracture in Japanese women." J Bone Miner Metab 26:79-85.

(Continued)

*Primary Examiner* — Craig Ricci
(74) *Attorney, Agent, or Firm* — Tanya A. Arenson; Casimir Jones, S.C.

(57) ABSTRACT

There is disclosed herein a method of increasing bone density, maintaining bone density and/or inhibiting loss of bone density and/or reducing osteochondral defects in an animal comprising administering to an animal an effective amount of a composition containing: vitamin K1, vitamin K2 or a mixture of vitamin K1 and vitamin K2, together with a physiologically acceptable carrier, incipient and/or diluent. Various compositions including vitamin K are also disclosed.

4 Claims, 1 Drawing Sheet

(56) References Cited

OTHER PUBLICATIONS

Valette et al., (2007), "Evolution of some biochemical markers of growth in relation to osteoarticular status in young horses: results of a longitudinal study in three breeds." Equ comp exer physiol 4(1):23-29.
Van Summeren et al., (2007) "Pronounced elevation of undercarboxylated osteocalcin in healthy children." Pediatr Res, 61(3):366-70.
Van Summeren et al., (2008), "Vitamin K status is associated with childhood bone mineral content." Br J Nutr. 100(4):852-8.
Vergnaud et al., (1997), "Undercarboxylated osteocalcin measured with a specific immunoassay predicts hip fracture in elderly women: the EPIDOS Study." J Clin Endocrinol Metab 82(3):719-724.
Vervuert et al., (2002) "Biochemical markers of bone activity in young standardbred horses during different types of exercise and training." J Vet Med A Physiol Pathol Clin Med, 49(8):396-402.
Yanagisawa et al., (2005), "Natto bacillus contains a large amount of water-soluble vitamin K (menaquinonE-7)." J Food Biochem 29:267-277.
Yoshida et al., (2008), "Phylloquinone intake, insulin sensitivity, and glycemic status in men and women." Am. J. of Clin. Nutri. 88(1):210-215.
Price, WA (1939), Nutrition and Physical Degeneration, Price-Pottenger Foundation La Mesa, CA.
Supplementary EP Search Report mailed Sep. 23, 2011, EP Patent Application No. EP09756955.
Olvera-Martinez, Blanca I., et al., "Preparation of Polymeric Nanocapsules Containing Octyl Methoxycinnamate by the Emulsification—Diffusion Technique: Penetration Across the Stratum Corneum", Journal of Pharmaceutical Sciences, vol. 94, No. 7, Jul. 2005, pp. 1552-1559.
Extract from Suttie J.W. (2009) Vitamin K in Health and Disease CRC Press Fl. USA, p. 142.
International Search Report mailed Aug. 26, 2009, PCT/AU2009/000693.
International Preliminary Report on Patentability dated Jul. 7, 2010, PCT/AU2009/000693.
Adams et al., (2005), "Vitamin K in the treatment and prevention of osteoporosis and arterial calcification." Am J Health Syst Pharm, 62(15):1574-81.
Allen, (2003), "Biochemical markers of bone metabolism in animals: Uses and limitations." Vet Clin Pathol. 32:101-113.
Bell et al., (2001), "Daily Access to pasture turnout prevents loss of mineral in the third metacarpus of Arabian weanlings." J Anim Sci, 79(5):1142-50.
Billinghurst et al., (2003), "Significant exercise-related changes in the serum levels of two biomarkers of collagen metabolism in young horses." Osteoarthritis Cartilage, 11(10):760-9.
Binkley et al., (2000), "Vitamin K supplementation reduces serum concentrations of under-gamma-carboxylated osteocalcin in healthy young and elderly adults." Am J Clin Nutr, 72(6):1523-8.
Bitensky et al., (1988), "Circulating vitamin K levels in patients with fractures." J Bone Joint Surg Br. 70(4):663-4.
Booth et al., (2003) "Vitamin K intake and bone mineral density in women and men." Am J Clin Nutr, 77(2):512-6.
Booth et al., (2004) "Associations between vitamin K biochemical measures and bone mineral density in men and women." J Clin Endocrinol Metab, 89(10):4904-9.
Suttie et al., (1998), "Vitamin K deficiency from dietary vitamin K restriction in humans." Am J Clin Nutr 47:475-480.
Braam et al., (2003), "Factors affecting bone loss in female endurance athletes: a two-year follow-up study." Am J Sports Med, 31(6):889-95.
Brandt, (2003), "Chondrocalcinosis, osteophytes and osteoarthritis." Ann Rheum Dis 62:499-500.
Caraballo et al., (1999), "Long-term use of oral anticoagulants and the risk of fracture." Arch Intern Med 159(15):1750-1756.
Carstanjen et al., (2005), "Serum osteocalcin and CTX-MMP concentration in young exercising thoroughbred racehorses." J Vet Med A Physiol Pathol Clin Med, 52(3):114-20.
Chiappe et al., (1999), "Influence of age and sex in serum osteocalcin levels in thoroughbred horses." Arch Physiol Biochem, 107(1):50-4.
Cockayne et al., (2006), "Vitamin K and the prevention of fractures: systematic review and meta-analysis of randomized controlled trials." Arch Intern Med, 166(12):1256-61.
Craciun et al., (1998), "Improved bone metabolism in female elite athletes after vitamin k supplementation." Int J Sports Med 19:479-484.
Donabedian et al., (2008), "Early changes in biomarkers of skeletal metabolism and their association to the occurrence of osteochondrosis in the horse." Equine Vet J 40(3):253-259.
Ensminger et al., (1990) "Feeds & Nutrition", 2nd Ed. Ensminger Publishing Co., Clovis, CA.
Ewing et al., (1943) "The ultraviolet absorption of vitamin k1 and the effect of light on the vitamin." J. Biol. Chem. 147:233-241.
Garber et al., (1999) "Comparison of phylloquinone bioavailability from food sources or a supplement in human subjects." J. Nutr. 129:1201-1203.
Gijsbers et al., (1996), "Effect of food composition on vitamin K absorption in human volunteers." Br J Nutr, 76:223-229.
Greer, (2004), "Vitamin K in human milk—still not enough." Acta Paediatr, 93(4):449-50.
Groenen-Van Dooren et al., (1995) "Bioavailability of phylloquinone and menaquinones after oral and colorectal administration in vitamin K-deficient rats." Biochem Pharmacol, 50(6):797-801.
Gundberg et al., (1998), "Vitamin K status and bone health: an analysis of methods for determination of undercarboxylated osteocalcin." J. of Clin. Endocri. and Metabol. 3:29.
Hauschka et al., (1989), "Osteocalcin and matrix gla protein: vitamin K-dependent proteins in bone." Physiol. Rev. 69(3):990-1047.
Hodges et al., (1991) "Depressed levels of circulating menaquinones in patients with osteoporotic fractures of the spine and femoral neck." Bone, 12(6):387-9.
Hodges et al., (1993), "Circulating levels of vitamins K1 and K2 decreased in elderly women with hip fracture." J Bone Miner Res 8(10):1241-5.
Hoekstra et al., (1999), "Comparison of bone mineral content and biochemical markers of bone metabolism in stall-reared vs. pasture-reared horses." Equine Vet J Suppl, 30(34):601-4.
Jackson et al., (2005), "Biochemical markers of bone metabolism and risk of dorsal metacarpal disease in 2-year-old Thoroughbreds." Equine Vet J, 37(1):87-89.
Kameda et al., (1996) "Vitamin K2 inhibits osteoclastic bone resorption by inducing osteoclast apoptosis." Biochem. Biophys. Res Commun. 220(3): 515-519.
Khosla et al., (2008), "Building bone to reverse osteoporosis and repair fractures." J.Clin. Invest. 118(2):421-428.
Knapen et al., (1998), "Correlation of serum osteocalcin fractions with bone mineral density in women during the first 10 years after menopause." Calcif Tissue Int 63(5):375-379.
Knapen et al., (2007), "Vitamin K2 supplementation improves hip bone geometry and bone strength indices in postmenopausal women." Osteoporos Int, 18(7):963-72.
Kojima et al., (2004), "Vitamin K concentrations in the maternal milk of Japanese women." Acta Paediatr, 93(4):457-63.
Luukinen et al., (2000), "Strong prediction of fractures among older adults by the ratio of carboxylated to total serum osteocalcin." J Bone Miner Res 15(12):2473-2478.
Marcus et al., (2007), "Cyclodextrin as pharmaceutical solubilizers." Adv. Drug Del. Rev. 59:645-666.
Mitchell et al., (2001), "Supplementation of rats with a lutein mixture preserved with vitamin E reduces tissue phylloquinone and menaquinone-4." Am. J. of Vit. and Nutri. Res. 71(1):30-5.
NRC ,(2007), "Nutrient Requirements of Horses." 6th Ed., National Academy Press, Washington DC.
O'Connor et al., (2007), "Serum percentage undercarboxylated osteocalcin, a sensitive measure of vitamin K status, and its relationship to bone health indices in Danish girls." British J. of Nutr. 97(4):661-4.

(56) References Cited

OTHER PUBLICATIONS

Price et al., (2001) "Biochemical markers of bone metabolism in growing thoroughbreds: a longitudinal study." Res Vet Sci 71(1):37-44.
Prynne et al., (2005), "Intake and sources of phylloquinone (vitamin k1) in 4-year-old British children: comparison between 1950 and the 1990s." Public Health Nutrition 8(2), 171-180.
Schurgers et al., (2000), "Determination of phylloquinone and menaquinones in food: effect of food matrix on circulating vitamin K concentrations." Haemostasis 30(6):298-307.
Schurgers et al., (2007), "Vitamin K2 improves bone strength in post-menopausal women." Int Congress Series 1297:179-187.
Schurgers et al., (2007), "Vitamin K-containing dietary supplements: comparison of synthetic vitamin K1 and natto-derived menaquinone-7." Blood, 109(8):3279-83.
Shea et al., (2007), "Role of Vitamin K in the regulation of calcification." Int Congress Series 1297:165-178.
Siciliano et al., (2000) "The effect of initiation of exercise training in young horses on vitamin K status." J Anim Sci, 78(9):2353-8.
Siciliano et al., (2000), "Changes in vitamin k status of growing horses." J Equi Vet Sc. 20(11): 726-729.
Koontz et al., "Stability of Natamycin and its cyclodextrin inclusion complexes in aqueous solution." J. Agric. Food Chem. 2003, 51(24):7111-7114.

* cited by examiner

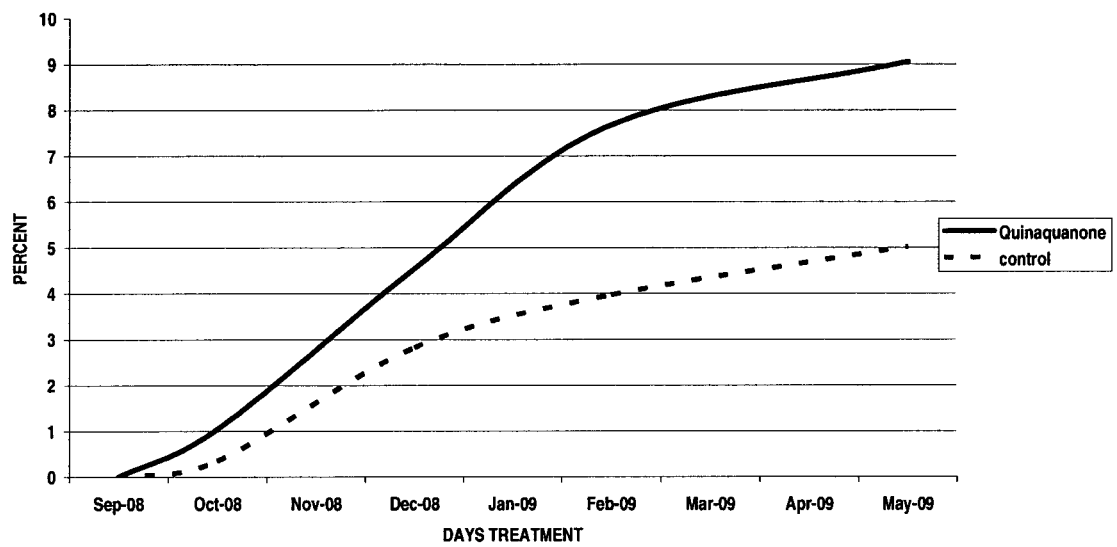

METHOD FOR INCREASING BONE DENSITY AND/OR REDUCING ANY OSTEOCHONDRAL DEFECTS IN AN ANIMAL AND A COMPOSITION INCLUDING VITAMIN K

TECHNICAL FIELD

The present invention relates to a method for increasing the bone density and/or reducing osteochondral defects in an animal and various compositions including vitamin K suitable for administration to an animal.

BACKGROUND OF THE INVENTION

The information provided herein and references cited are provided solely to assist the understanding of the reader, and do not constitute an admission that any of the references or information is prior art to the present invention.

Bones are rigid organs forming part of the endoskeleton of vertebrate animals. They function to move, support, and protect various organs of the body, produce red and white blood cells and store minerals. Bones come in a variety of shapes and have a complex internal and external structure. They are strong, hard and lightweight.

Bone is a dynamic tissue, constantly remodeling itself in response to the forces of impact and loading. Bones are made up of two types of bone tissue, cortical bone and trabecular bone. Cortical bone is the dense bone that gives bones their shape and strength. It makes up about 80% of the adult skeleton. Trabecular bone is a 'mesh like' or honeycomb bone that forms in the ends of the long bones surrounding the bone marrow.

Serious bone injuries are generally attributed to normal bone reacting to abnormal circumstances however this is often not the case. Bone injuries can be caused through abnormal bone reacting to normal impact and loading. Many bone injuries result from areas of weakened bone along with small stress fractures that predispose the bone to more serious injury. For example osteoporosis is a consequence of an imbalance between bone formation and resorption of bone. Increasing bone density or building stronger bone is vital in order to prevent serious bone injury.

It would be desirable to provide methods of increasing bone density in an animal so as to prevent bone injury and to provide compositions suitable for the same.

SUMMARY OF THE INVENTION

According to a first aspect of the present invention, there is provided a method of increasing bone density, maintaining bone density and/or inhibiting loss of bone density and/or reducing osteochondral defects in an animal comprising administering to an animal an effective amount of a composition containing:
vitamin K1, vitamin K2 or a mixture of vitamin K1 and vitamin K2, together with a physiologically acceptable carrier, excipient and/or diluent.

According to a second aspect of the present invention, there is provided a method of increasing plasma level of vitamin K in an animal beyond that achievable by diet comprising administering a composition including vitamin K1, vitamin K2 or a mixture of vitamin K1 and vitamin K2, together with a physiologically acceptable carrier, excipient and/or diluent.

According to a third aspect of the present invention, there is provided a method of increasing bone density, maintaining bone density and/or inhibiting loss of bone density and/or reducing osteochondral defects in an animal comprising:
administering a composition containing vitamin K1, vitamin K2 or a mixture of vitamin K1 and vitamin K2, together with a physiologically acceptable carrier, excipient and/or diluent and with or without an adjunct vitamin or mineral, to reach about the maximum achievable level of carboxylated osteocalcin in the animal being treated.

According to a fourth aspect of the present invention, there is provided a composition comprising:
vitamin K1, vitamin K2 or a mixture of vitamin K1 and vitamin K2; and
a UV absorber.

According to a fifth aspect of the present invention, there is provided a stable and water soluble composition comprising:
vitamin K1, vitamin K2 or a mixture of vitamin K1 and vitamin K2;
beta-carotene; and
an emulsifier and/or thickening agent.

According to a sixth aspect of the present invention, there is provided a stable powder composition comprising:
vitamin K1, vitamin K2 or a mixture of vitamin K1 and vitamin K2; and
beta-carotene;
an emulsifier and/or thickening agent;
encapsulated into a starch and/or a zeolite and/or
diluted by a diluent.

According to a seventh aspect of the present invention, there is provided a stable powder composition comprising
vitamin K1, vitamin K2 or a mixture of vitamin K1 and vitamin K2;
beta-carotene;
Vitamin D2 or D3 or a mixture of Vitamin D2 and D3;
an emulsifier and/or thickening agent;
encapsulated into a starch and/or a zeolite and/or
diluted by diluent.

According to an eighth aspect of the present invention, there is provided a stable powder composition comprising:
vitamin K1, vitamin K2 or a mixture of vitamin K1 and vitamin K2;
beta-carotene;
Vitamin D2 or D3 or a mixture of vitamin D2 and D3;
an emulsifier and/or thickening agent;
a mineral active;
encapsulated into a starch and/or a zeolite and/or diluted by a diluent being a mixture of monosaccharide or disaccharide and starch.

According to a ninth aspect, there is provided a horse supplement or horse feed comprising the composition of the fourth, fifth, sixth, seventh or eighth aspect.

DEFINITIONS

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

DESCRIPTION OF DRAWINGS

FIG. 1 is a graph of percentage change in radiographic bone density in 26 two year old yearlings administered with a formulation of the invention, named Quinaquanone™.

DETAILED DESCRIPTION OF PREFERRED EMBODIMENTS OF THE INVENTION

It was previously thought that horses as herbivores obtain sufficient vitamin K for their needs from consuming green fresh grasses and humans as omnivores consuming vegetables and dairy products. The present inventors however have discovered for the first time and contrary to popular belief that horses with low bone mineral density are vitamin K deficient reflecting a low dietary intake. The present inventors have discovered that it is possible to increase plasma levels of vitamin K in horses not achievable by consuming natural grasses by administering a composition including vitamin K. Having regard to the above:

(a) researchers have been looking at bone metabolism in horses, specifically the vitamin K dependent osteocalcin since 1993 and it has never occurred to any researchers that vitamin K has anything to do with it;

(b) major horse nutrition texts, including the 2 "bibles" (Ensminger M. E., Oldfield J. E. and Heinemann W. W., (1990) *Feeds & Nutrition* 2nd Ed., Ensminger Publishing Co., Clovis Calif.; and NRC (2007) *Nutrient Requirements of Horses*, 6th Ed., National Academy Press, Washington D.C.) state that vitamin K is plentiful in horse food. In addition the only actual measurement of vitamin K in horse food has also been reported incorrectly. Siciliano P. D., Warren L. K. and Lawrence L. M., (2000) *Changes in vitamin K status of growing horses*. J. Equi Vet. Sc. 20 (11): 726-729 mistakenly report the amount of "vitamin K status of horse freely consuming 261 mg/day Phylloquinone per 100 gm dry food in a primary forage diet" which should have read 261 µm/day as analysed and confirmed by the inventors, and which is 1000 times less than that reported by Siciliano et al. The inventors on contacting the laboratory who did the test were able to confirm that the amount quoted is incorrect. As a result of these references, the question of vitamin K deficiency in horses has not been questioned, until this discovery and the false assumption that horses get plenty of vitamin K from their diet has been perpetuated.

(c) The inventors have discovered that most horse diets are in fact vitamin K deficient.

The present inventors have also discovered that high bone mineral density (BMD) is significantly correlated with (1) lower VRL (visible radiographic lesions), (2) reduced incidence of dorsal metacarpal disease (DMD) and (3) high VK (vitamin K) status.

Vitamin K (VK) is widely associated with three long-established misconceptions: (a) coagulation has the greatest requirement for VK; (b) green leaves (leafy vegetables) and forages provide surplus VK for either humans or herbivores; and (c) hindgut microflora provide sufficient VK to prevent deficiency.

Vitamin K (VK) has therefore long been "taken as sufficient" in human and animal nutrition, since the amount in foods and feeds or faeces is obviously sufficient to avoid coagulopathy. This however is not the case. In this regard, the requirement for VK1 was established by IV injections to vitamin K deficient humans so as to maintain normal prothrombin times. The Recommended Dietary Allowance RDA is 0.5-1.0 µg/kg of bodyweight (NRC, 1989). To achieve the RDA from a dietary intake is however difficult as the bioavailability from green vegetable matter is around 10% and there are recommendations that the levels of Vitamin K intake should be increased to 0.5-1 mg/day.

Many diets (human and animal) are therefore in fact VK deficient. Epidemiological studies on children from Denmark and Holland have shown a pronounced elevation of uncarboxylated osteocalcin in healthy children O'Connor E, Molgaard C, Michaelsen K. F. Jakobsen J, Lamberg-Allardt C. J. E, Cashman K. D. British Journal of Nutrition 2007, 97: 661. See also Summeren M. V. Braam L, Noirt F, Kuis W, Vermeer C. Pediatric Research 2007, 61: 366

Deficiency of VK resulting in haemorrhagic disease is rare, since the clotting factors require so little of it. The non-coagulation VK dependent proteins however require much higher intake, and sub-clinical deficiency is widespread. The major non-coagulation diseases to which VK deficiency is either a primary or contributory cause include osteoporosis, osteochondral defects, chondrodysplasia and atherosclerosis. It has been found by the present inventors that vitamin K is not abundantly available in most modern diets for humans, dairy cows or horses.

Biochemically, VK has 3 known functions: the major is as cofactor in correct formation of special proteins including Osteocalcin, MGP (Matrix Gla Protein), Protein C and Protein S. The latter two (coagulation) roles can be performed by K1, K2 or K3, but Osteocalcin (bone) and MGP (cartilage, arteries etc.) are only activated by K1 and K2. K1 and K2 also inhibit osteoclast activity, and activate an SXR gene for formation of bone collagen.

Also recent evidence suggests a potential beneficial role of Vitamin K in glucose homeostatis, insulin sensitivity and energy metabolism: Yoshida M., Booth S. L., Meigs J. B., Salzman E., Jacques P. F. American Journal of Clinical Nutrition 2008, 88: 210.

Phylloquinone (K1) is an integral part of respiration in the chloroplasts of green leaves. The concentration of K1 in leaves is closely correlated to the concentration of chlorophyll. Non-photosynthetic parts of plants (stalks & seeds) contain negligible K1 e.g. oats 0.02 mg/kg.

Degradation of K1 begins rapidly as soon as photosynthesis ceases and the rate of degradation is directly related to the intensity of UVB. Pure K1 in solution is denatured in 20 minutes in direct sunlight. K1 in pasture/forage plants has a half-life of 6-7 hours in direct sunlight. The natural bioavailability of K1 is around 8-10% and when consumed with fat is 15-16% of the apparent concentration in the leaf. Aside from the degradation of K1, a further problem herbivores have is that the concentration of other fat soluble nutrients such as lutein in green vegetation may be up to 100 times higher than the concentration of vitamin K1. Lutein competes with the absorption and metabolism of vitamin K1 (see Mitchell G. V, Cook K. K., Jenkins M. Y, Grundel E International Journal of Vitamin and Nutrition Research 2001, 71: 30) as well as high levels of Vitamin E (see Tovar A, Ameho C. K. Blumberg J. B., Peterson J. W, Smith D, Booth S. Nutrition And Metabolism 2006, 3:29) and therefore with the combination of UV, the plant matrix and competition with other fat soluble vitamins, the actual amount of vitamin K1 available is much less than quoted or expected. It follows that the vitamin K requirement for animals and humans has been grossly underestimated resulting in vitamin K deficiency.

Menaquinone (K2) is produced by mammals by conversion of K1. In human diets it is found in fermented food (cheese, natto) and animal fats (mainly in dairy products such as milk fat), but only in significant amounts in the fat produced by animals grazing fresh green pasture. The capacity for herbivores to pick up K2 is small. For example, the milk fat of grain/hay fed cows contains only a fraction of the K2 of that in the milk of pasture fed cows, which is seasonal, according to the greenness of the pasture. K2 is also produced by microbes (principally family bacillaceae) for their own respiration. Many of these are normal hindgut microflora, hence the relatively consistent finding of VK in the faeces of herbivores and omnivores. The remarkable results from natto in prevention/treatment of osteoporosis, reduction of fracture risk, improved bone geometry and cartilage strength (see Yanagisawa Y and Sumi H., (2005) *Natto Bacillus contains a large amount of water-soluble vitamin K (Menoquinone*-7) J. Food Biochem 29:267-277) is likely due to the stable, water soluble form of Vitamin K2 within it. Trials by the present inventors show that stabilized water soluble K1 and K2 composition in accordance with the present invention produces over twice the VK plasma levels in an animal as the same amount of K1 in oil.

Menadione (K3) is a synthetic quinone which has partial VK activity. It activates the coagulation proteins, but not Osteocalcin or MGP. It has been banned by FDA for inclusion in human foods and supplements, and is unpopular in pet-foods, due to its toxicity. It is cytotoxic, an aggressive pro-oxidant, antagonizes vitamin E, and inhibits calcium uptake. Its use will probably be restricted to short-lived animals (e.g. broilers and porkers).

The proliferation of VK deficiency in human nutrition (and probably the concomitant increase in osteoporosis and atherosclerosis) over the last 50 years has four obvious epidemiological explanations: (1) obsolescence of home-grown vegetables and a general decrease in consumption of green vegetables in the last 40 years (for example from 39 µg/day to 24 µg/day in British children—see Prynne C. J. Thane C. W., Prentice A, Wadsworth M. E. J. Public heath Nutrition 2005 8: 171); (2) exposure of leafy greens to supermarket fluorescent light; (3) promotion of low-fat/low-cholesterol diets; and (4) predominance of intensive (rather than pasture) dairy management.

The perpetuation of the misconception that herbivores receive sufficient VK from hindgut microflora is dependent on coprophagy. VK is not absorbed from the hindgut. Since a fat-soluble vitamin needs bile salts for absorption, and bile salts are only in the foregut, this should be obvious. Laboratory animals fed VK-free diets have normal prothrombin times, but when coprophagy is rigorously prevented, develop severe haemorrhagic disease within 2 weeks. Management practices which minimize or eliminate coprophagy (such as parasite control in horses) make the hindgut source of VK negligible.

Tests by the present inventors show that VK is not abundantly bioavailable in most modern diets, either for humans, dairy cows or horses. Nutrition text figures which have passed down the assumption that VK is abundant in leafy greens/forages/hay appear to have been estimated before accurate analytical methods were developed, and seem to disregard the instability and poor bioavailability of natural K1 in green grasses and vegetables. The inventors have for the first time demonstrated that the level of uncarboxylated osteocalcin is low in horses with visual signs of bone mineral density and which reflects vitamin K deficiency.

Horse requirement of bioavailable VK appears to be comparable to other species, i.e. around 15-20 µg/kg bwt/day. Some species require higher levels. This can be provided by a diet totally of high quality deep green pasture, which is rarely possible in Australia and other countries. A diet of pasture, hay and concentrates falls short unless specifically supplemented by administration of vitamin K as taught by the present invention. The many non-coagulation functions of K1 may provide a scientific explanation for the traditionally honoured benefit of "rest at pasture".

For horses dietary vitamin K supplementation along with careful design of training programs will result in improved bone density and/or reduced osteochondral defects and in turn, improved skeletal durability. Young horses will able to stay in training for longer without the interruptions that bone injuries can cause.

Having regard to the above, the present invention provides a method of increasing bone density, maintaining bone density and/or inhibiting loss of bone density and/or reducing osteochondral defects in an animal comprising administering to an animal an effective amount of a composition containing:

vitamin K1, vitamin K2 or a mixture of vitamin K1 and vitamin K2, together with a physiologically acceptable carrier, excipient and/or diluent.

The present invention also provides a method of increasing plasma level of vitamin K in an animal beyond that achievable by diet comprising administering a composition including vitamin K1, vitamin K2 or a mixture of vitamin K1 and vitamin K2, together with a physiologically acceptable carrier, excipient and/or diluent.

The composition may further contain one or more adjunct vitamins or minerals. Suitable adjunct vitamins include Vitamin D2, Vitamin D3 and suitable minerals include silica, boron, magnesium, calcium and/or phosphorus.

In one embodiment the plasma level is achieved by supplementing the diet of the animal with vitamin K. In one embodiment, the plasma levels attained cannot be achieved by usual intake of food and drink of the animal such as by eating leafy greens and vegetables irrespective of the amount consumed.

The present invention also provides a method of increasing bone density, maintaining bone density and/or inhibiting loss of bone density and/or reducing osteochondral defects in an animal comprising:

administering a composition containing vitamin K1, vitamin K2 or a mixture of vitamin K1 and vitamin K2, together with a physiologically acceptable carrier, excipient and/or diluent and with or without an adjunct vitamin or mineral, to reach about the maximum achievable level of carboxylated osteocalcin in the animal being treated.

In one embodiment the method may further comprise determining the carboxylated osteocalcin level in the bone of the animal prior to administering the vitamin K composition and administering the composition if the carboxylated osteocalcin level is below the maximum achievable level of carboxylated osteocalcin in the animal being treated.

The animal can be a human, bovine, equine, canine, ovine, porcine, avian, feline, rodent or other vertebrate. In one embodiment the animal is a horse.

The composition can be administered orally, topically, parenterally, intramuscularly, by injection, transmucosally, transdermally, intranasally, by inhalation or intravenously. The composition can be in the form of a slow-release composition.

Also provided are composition containing vitamin K.

A composition according to one embodiment comprises:

vitamin K1, vitamin K2 or a mixture of vitamin K1 and vitamin K2; and a UV absorber.

The composition may further comprise an emulsifier and/or thickener.

The composition may further comprise an adjunct vitamin such as Vitamin D2 and/or Vitamin D3.

The composition may further comprise a diluent. A suitable diluent may be a mixture of monosaccharide and/or disaccharide, and starch The composition may also comprise a mineral active such as silica and/or boron A composition according to one embodiment is a stable and water soluble composition comprising:

vitamin K1, vitamin K2 or a mixture of vitamin K1 and vitamin K2;

beta-carotene; and an emulsifier and/or thickening agent.

The composition may further comprise a diluent. A suitable diluent may be a mixture of monosaccharide and/or disaccharide, and starch.

The composition may also comprise a mineral active such as silica and/or boron.

In one embodiment the composition is in the form of a liquid or a paste.

A composition according to another embodiment is a stable powder composition comprising:
vitamin K1, vitamin K2 or a mixture of vitamin K1 and vitamin K2; and
beta-carotene;
an emulsifier and/or thickening agent;
encapsulated into a starch and/or a zeolite and/or
diluted with a diluent.

The diluent may be a mixture of monosaccharide and/or disaccharide, and starch.

The powder composition may further comprise a mineral active. The mineral active may be silica and/or boron.

A composition according to another embodiment is a stable powder composition comprising
vitamin K1, vitamin K2 or a mixture of vitamin K1 and vitamin K2;
beta-carotene;
Vitamin D2 or D3 or a mixture of Vitamin D2 and D3;
an emulsifier and/or thickening agent;
encapsulated into a starch and/or a zeolite and/or
diluted by a diluent.

The diluent may be a mixture of monosaccharide and/or disaccharide, and starch.

The powder composition may further comprise a mineral active. The mineral active may be silica and/or boron.

A composition according to another embodiment is a stable powder composition comprising:
vitamin K1, vitamin K2 or a mixture of vitamin K1 and vitamin K2;
beta-carotene;
Vitamin D2 or D3 or a mixture of Vitamin D2 and D3;
an emulsifier and/or thickening agent;
a mineral active;
encapsulated into a starch and/or a zeolite and/or diluted by a diluent being a mixture of monosaccharide and/or disaccharide, and starch.

The mineral active may be silica and/or boron.

In one embodiment, the vitamin K from the powder compositions is soluble when added to water.

Also provided is a horse supplement or horse feed comprising a composition of the invention.

Vitamin K1, vitamin K2 or combination of vitamin K1 and K2 may be present in an amount of from 0.01 wt % up to 99.9 wt % of the composition, for example up to 95 wt %, up to 90 wt %, up to 80 wt %, up to 70 wt %, up to 60 wt %, up 50 wt %, up to 40 wt %, up to 30 wt %, up to 20 wt %, up to 15 wt %, up to 10 wt %, up to 5 wt %, up to 1.5 wt %, up to 0.5 wt %, up to 0.2 wt %, up to 0.15 wt % or up to 0.1 wt %.

The composition may include a UV absorber. The UV absorber may be a zinc oxide, lycopene, lutein or beta-carotene. The composition may also include vitamin D2 and/or D3. In one embodiment the UV absorber is present in an amount of 1/10th the concentration of vitamin K1 and/or vitamin K2. In one embodiment vitamin D2 and/or D3 is present in an amount of 3 times the concentration of vitamin K1 and/or vitamin K2.

The UV absorber and vitamin D2 and/or vitamin D3 may be present in respective amounts up to 10 wt %, for example up to 5.0 wt %, up to 3.0 wt %, up to 2.0 wt %, up to 1.5 wt %, up to 1.0 wt %, up to 0.5 wt %, up to 0.25 wt %, up to 0.2 wt %, up to 0.15 wt %, up to 0.1 wt % or up to 0.01 wt %.

The composition may include a suitable excipient or diluent which may be a mixture of monosaccharides and/or disaccharides or a mixture of monosaccharides and/or disaccharides with starch which may be present in amounts up to 99 wt %, for example up to 95 wt %, up to 90 wt %, up to 80 wt %, up to 70 wt %, up to 60 wt %, up to 50 wt %, up to 40 wt %, up to 30 wt %, up to 20 wt %, up to 15 wt %, up to 10 wt %, up to 5 wt %, up to 1.5 wt %, up to 0.5 wt %, up to 0.2 wt %, up to 0.15 wt % or up to 0.1 wt %.

The active mineral may be a soluble mineral such as silica and/or boron. The active mineral may be present in an amounts up to 5.0 wt %, for example 3.0 wt %, 2.0 wt %, 1.5 wt %, 1.0 wt %, 0.5 wt %, 0.25 wt %, 0.2 wt % or 0.15 wt %.

In one embodiment the composition may be in the form of a liquid, paste or powder. The composition may be in the form of a beverage, soup, concentrate, suspension, emulsion, pill, granules, tablets, capsules, suppository, controlled-release composition, cream, ointment, salve, lotion, aerosol or wafer. The composition may be added to animal feed.

The composition may be administered daily or twice daily or more or less frequently in a single dose or in several doses.

The composition may include a weight ratio of K1:K2 of 0.1:9.9 to 9.9:0.1, for example from 1:9 to 9:1, 2:8 to 8:2, 3:7 to 7:3, 4:6 to 6:4 or 5:5.

In one embodiment, there is provided a stable and water soluble powder composition comprising:
vitamin K1, vitamin K2 or a mixture of vitamin K1 and vitamin K2;
beta-carotene encapsulated into a starch and/or a zeolite.

The starch may be any of the cyclodextrins (such as alpha, beta, gamma or modified cyclodextrin), amylose or amylopectin. The starch may be sourced from potatoes, wheat, corn or rice or other plant containing starch. The zeolite may be any hydrated aluminosilicate mineral such as analcine, chabazine, heulandite, natrolite, phillipsite and stilbite. By encapsulating the composition into the starch and/or a zeolite, the composition is UV stable and there is no discolouration. In oil the composition tends to go black with no loss of activity. In one embodiment there is binding within the lipophilic portion of the starch. In another embodiment there is binding within the pores of the zeolite.

A diluent may be present. Suitably the diluent is a sugar. The sugar can be any sugar monosaccharide or disaccharide.

The composition can include organic or inorganic carriers, excipients and/or diluents. Additives may include emulsifiers/surfactants, thickeners, preservatives, solubilisers, fumed silica or vitamin D3 (cholecalciferol), sweeteners or other suitable additive as desired. Vitamin D3 is desirable for bone mineral metabolism as is silica and boron.

Suitable thickeners include polyethylene glycol 4000 or any of the gums such as xanthan gum and guar gum. Thickeners may be included in amounts up to 99.9 wt %, for example up to 95 wt %, up to 90 wt %, up to 80 wt %, up to 70 wt %, up to 60 wt %, up 50 wt %, up to 40 wt %, up to 30 wt %, up to 20 wt %, up to 15 wt %, up to 10 wt %, up to 5 wt %, up to 1.5 wt %, up to 0.5 wt %, up to 0.2 wt %, up to 0.15 wt % or up to 0.1 wt %.

Suitable emulsifiers include those having E numbers of E400-E500 such as polyethoxylated castor oil (PEG 35) or TWEEN 80 (polysorbate 80).

Emulsifiers may be included in amounts up to 99.9 wt %, for example up to 95 wt %, up to 90 wt %, up to 80 wt %, up to 70 wt %, up to 60 wt %, up 50 wt %, up to 40 wt %, up to 30 wt %, up to 20 wt %, up to 15 wt %, up to 10 wt %, up to 5 wt %, up to 1.5 wt %, up to 0.5 wt %, up to 0.2 wt %, up to 0.15 wt % or up to 0.1 wt %.

Suitable preservatives include methyl paraben. Preservatives may be included in amounts up to 2 wt %, for example up to 1 wt % or up to 0.5 wt %.

Suitable solubilisers include ethanol, propylene glycol, polyethylene glycol 400, glycerol, or isopropyl alcohol. Solubilisers may be included in an amount up to 99.9 wt %, for example up to 95 wt %, up to 90 wt %, up to 80 wt %, up to 70 wt %, up to 60 wt %, up 50 wt %, up to 40 wt %, up to 30 wt %, up to 20 wt %, up to 15 wt %, up to 10 wt %, up to 5 wt %, up to 1.5 wt %, up to 0.5 wt %, up to 0.2 wt %, up to 0.15 wt % or up to 0.1 wt %.

Suitably the composition is UV stable and has improved bioavailability.

Other additives may include buffers, antioxidants or sweeteners such as mono and disaccharides, and starch.

In one embodiment, for at least every 7 mg of K1 or at least every 7 mg of K2 or for any ratio of K1 and K2 when present there is provided optionally 20 mg Vitamin D3 (500,000 iu/gm) water soluble powder and at least 7 mg beta carotene 10% water soluble powder.

The composition may be packaged in a syringe as a paste

The invention will now be described by way of example only having regard to the following examples.

EXAMPLE 1

The present inventors conducted an analysis of vitamin K present in hay. The vitamin K1 content of forage samples was determined from lush green improved pasture in March. The results are shown in the following table.

| | Vitamin K1 content of forage samples mg/kg. Fresh samples (leaves only). | | | | | | | |
|---|---|---|---|---|---|---|---|---|
| | 1. Clover freshly cut | 2. Kikuyu freshly cut | 3. Lucerne hay | 4. *Phalaris* freshly cut | 5. Rye freshly cut | 1 + 4 + 5 mix fresh | 1 + 4 + 5 mix 2 days old | 1 + 4 + 5 mix shed 2 week |
| Vitamin K1 | 2.26 | 2.74 | 3.03 | 2.93 | 1.93 | 2.39 | 1.93 | 1.65 |
| Water % | 84.9 | 82.6 | 9.1 | 82.1 | 78.2 | 81.7 | 15.4 | 14.8 |
| Vitamin K1 Dry matter basis | 15.0 | 15.7 | 3.3 | 16.4 | 8.9 | 13.1 | 2.28 | 1.93 |

It can be seen from the above table that the hay used contained between 3.3 to 15 mg/kg of vitamin K1 on a dry matter basis when freshly cut but this amount drops significantly over time.

This was confirmed by two further tests on fresh phalaris and various other grasses as shown in the attached table:

| Decay of VK1 (mg/kg) in fresh *phalaris* | | | | Decay of VK1 (mg/kg) in fresh grass after 7 hours sunlight at different daily peak UV Index (PUVI) | | | | |
|---|---|---|---|---|---|---|---|---|
| cut at 11.00 hrs related to UV Index in March | | | | | | K1 | K1 | % |
| Time | 11.00 | 14.00 | 16.00 | 18.00 | Grass | PUVI | 0 hrs | 7 hrs | decay |
| UVI | 3 | 5 | 2.5 | 0.5 | Prairie | 2 | 2.1 | 1.5 | 29 |
| VK | 3.5 | 2.7 | 2.2 | 1.9 | *Phalaris* | 5 | 3.5 | 1.9 | 46 |
| | | | | | Couch | 6 | 3.1 | 1.4 | 60 |
| | | | | | Rhodes | 7 | 3.6 | 1.4 | 62 |

The results show that over time there is a significant reduction in vitamin K1 in hay and therefore administration of cut hay does not provide a surplus vitamin K amount which is contrary to the general assumption in animal nutrition publications that hay provides surplus vitamin K. It is therefore clear that it is necessary to supplement a hay diet with administration of vitamin K in order to obtain the horse requirement of bioavailable VK.

EXAMPLE 2

This example shows that high bone mineral density (BMD) in horses can be correlated with reduced incidence of both dorsal metacarpal disease in young racehorses and visible radiographic lesions (VRL) in yearlings.

Radiographic Bone Aluminium Equivalence (RBAE) was measured on lateral view of the left 3rd metacarpal of sixty-nine thoroughbred yearlings. The results are shown in the following table.

| Clinical Evaluation | Bone Mineral Density | Number |
|---|---|---|
| No visible lesions | 23.6 ± 1.2 (21.9-26.8) | 26 |
| One or more visible lesions | 22.3 ± 1.1 (20.4-24.1) | 43 |

The results show that bone mineral density can be correlated with visual radiographic lesions.

The VK dependent protein Osteocalcin (OC), produced by osteoblasts, is the major non-collagen protein in bone structure. Osteolysis or bone resorption (occurring continually alongside bone deposition in development) releases OC. OC is a marker of bone activity, rather than of bone formation. Carboxylation of OC is essential to normal osteogenesis, its percentage or ratio used as an indicator of bone integrity and vitamin K status in humans.

The determination of carboxylation of OC in horses was conducted. Carboxylated and under-carboxylated osteocalcin (OC) was measured in fourteen yearlings (Takara EIA Kits MK122 & MK121). The results are as shown in the following table:

| Clinical Evaluation | % Carboxylated OC | Number |
|---|---|---|
| No visible lesions | 86 ± 6.4 (77-92) | 5 |
| One or more visible lesions | 69 ± 10.8 (57-88) | 9 |

The horses were also tested using another osteocalcin kit (Metra Osteocalcin by Quidel Corporation) which measures total osteocalcin. The uncarboxylated osteocalcin was measured by precipitating the osteocalcin with barium sulphate (Grundberg C. M Nieman S. D Abrams S Rosen H. Journal of Clinical Endocrinology and Metabolism 1998, 83, 3258).

It can be seen from the table that a high percentage of under-carboxylated OC (or lower percentage of carboxylated OC) results in lesions and is therefore an indicator of Vitamin K deficiency. VRL scores were taken from standard yearling radiographs of the same horses. High BMD had a significant direct correlation with lower VRL (P<0.05), and high Vitamin K status (P<0.01).

The carboxylated OC levels of the fourteen yearlings were then determined having been subjected to three different environments, namely a paddock in late winter and under local drought, a paddock in spring one week after 80 mm rain and stabled over four weeks. In addition carboxylated levels of the fourteen yearlings were determined with the horses contained within different paddocks on the same farm. The results are shown in the following tables:

|  | % Carboxylated OC | Number |
|---|---|---|
| Environmental Situation |  |  |
| Late winter (local drought) | 75 ± 12.3 (57-92) | 14 |
| Spring one week after 80 mm rain | 90 ± 2.2 (87-93) | 14 |
| Stable for two weeks | 62 ± 14.8 (38-86) | 14 |
| Paddock Aspect |  |  |
| North-East | 88 ± 5.4 (82-92) | 3 |
| South-West | 73 ± 11.6 (58-88) | 6 |
| South | 70 ± 12.1 (57-88) | 5 |

Carboxylated OC levels and therefore Vitamin K status were significantly better (P<0.01) in the paddock with the most sunshine (the north-east aspect) and when the spring grass was well grown (P<0.01).

It can be seen from the above that Vitamin K is not abundantly available in most modern diets for horses. Pasture access has been shown to be beneficial to bone development in growing horses, in most studies as a contrast to stall confinement. Confinement also means a diet of hay and concentrates, deficient in vitamin K. In addition to free exercise, pasture access may in many cases provide a needed source of vitamin K.

EXAMPLE 3

Fourteen thoroughbred yearlings were provided with a supplement to normal pasture grazing. Four yearlings were supplemented with a blank paste as placebo. Five were supplemented with vitamin K in oil and five were supplemented with soluble vitamin K compositions in accordance with the present invention. Serum vitamin K in the yearlings was then determined:

| TB yearlings | VK serum ng/ml | Number |
|---|---|---|
| Blank paste + pasture | 12.0 ± 5.0 | 4 |
| 7 mg Vitamin K in oil + pasture | 20 ± 5.7 | 5 |
| 7 mg Vitamin K soluble + pasture in accordance with the present invention | 45 ± 4.8 | 5 |

Carboxylation levels were then determined on those provided with soluble VK and compared with those on placebo after 60 days. The results are as follows:

| TB yearlings 7 mg/day Vitamin K soluble | % Carboxylation OC | Number |
|---|---|---|
| Test group pre-supplement | 65 ± 12.7 (58-82) | 3 |
| Placebo group pre-supplement | 67 ± 10.1 (57-76) | 3 |
| Test group after 60 days 7 mg/day | 90 ± 2.2 (88-92) | 3 |
| Placebo group after 60 days | 69 ± 5.9 (64-75) | 3 |

It can be seen that administration of vitamin K improved vitamin K serum levels. Supplementation with a water-soluble and stabilised VK significantly (P<0.01) changed serum levels in the horses, and significantly (P<0.01) raised carboxylation in horses after 60 days. Supplementation with bio-available VK has the potential to provide a safe, effective and economical means of reducing the incidence of orthopaedic disease in horses. The measurements show that VK is not abundantly available in most modern horse diets.

The following examples show compositions suitable to make a stable therapeutic dose.

Water Soluble (WS) Compositions

EXAMPLE 4

| PASTE COMPOSITION | |
|---|---|
| 15 gm | Vitamin K1 and/or K2 |
| 11.8 Kg | Propylene glycol |
| 7.0 Kg | Polyethylene glycol 4000 |
| 850 gm | Polyethoxylated castor oil (PEG35) or TWEEN 80 |
| 15 gm | beta carotene WS10% |
| 105 gm | Vitamin D3 (500,000 iu/gm) WS |
| 100 gm | methyl paraben. |

EXAMPLE 5

| PASTE COMPOSITION | |
|---|---|
| 35 gm | Vitamin K1 and/or K2 |
| 9.4 Kg | Propylene glycol |
| 9.4 Kg | potable water |
| 105 gm | Polyethoxylated castor oil (PEG35) or TWEEN 80 |
| 35 gm | Beta carotene WS10% |
| 80 gm | Vitamin D3 (500,000 iu/gm) WS |
| 100 gm | methyl paraben |
| 660 gm | Xanthan Gum. |

EXAMPLE 6

| PASTE COMPOSITION | |
|---|---|
| 35 gm | Vitamin K1 and/or K2 |
| 9.4 Kg | Propylene glycol |
| 9.4 Kg | potable water |
| 105 gm | Polyethoxylated castor oil (PEG35) or TWEEN 80 |
| 35 gm | Beta carotene WS10% |
| 100 gm | methyl paraben |
| 660 gm | Xanthan Gum. |

EXAMPLE 7

| LIQUID COMPOSITION | |
|---|---|
| 15 gm | vitamin K1 and/or K2 |
| 5 Kg | Polyethoxylated castor oil (PEG35) or TWEEN 80 |
| 15 Kg | Ethanol 100% |
| 15 gm | beta carotene WS10% |
| 105 gm | Vitamin D3 (500,000 iu/gm) WS |
| 100 gm | methyl paraben. |

EXAMPLE 8

Stable Powder Composition Concentrate (A)

5 Kg of vitamin K1 and/or K2 was added to 10 Kg beta cyclodextrin and ethanol when required and heated to 40° C. in a mixer for an amount of time for the clathrate to be incorporated i.e., until the vitamin K1 and/or K2 became incorporated into the hydrophobic portion of the clathrate, and then dried. The cyclodextrin may be replaced with a linear starch and in this case the amylose starch is a linear coil and the K1 and/or K2 becomes incorporated within the coil. The cyclodextrin may be replaced with a zeolite and the K1 and/or K2 becomes incorporated in the pores of the zeolite. 5 Kg emulsifiers and/or thickening agents (suitably E numbers E400-E500) is added and 5 Kg of Beta carotene (10% WS) is added. To the composition is added 2 Kg (Silica)Aerosil 200 by coating the outside of the particles to form a free flowing powder.

EXAMPLE 9

Stable Powder Composition Concentrate (B) Preblend

7 Kg of Vitamin K1 and/or K2
21 Kg Polyethoxylated castor oil (PEG35emulsifiers)
5 Kg of Beta carotene (10%)
464 Kg Icing sugar 5% cornstarch

EXAMPLE 10

23 Kg of the above preblend (Example 9) was mixed with 745 gm of vitamin D3 (500,000 IU/gm WS) and made up to 464 Kg with icing sugar having a Vitamin K1 or K2 concentration of 7 mg/10 gm 26 two-year old thoroughbred racehorses at commencement of training for racing were divided into two groups. One group ("quinaquanone") received the 7 mg Vitamin K formulation each day in feed for six months. The other group ("control") received an apparently identical powder containing no Vitamin K. Digital radiographs of the left third metacarpal bone and an adjacent aluminium stepwedge were taken at various intervals. The radiographic density of the bone and the stepwedge were measured and RBAE (radiographic bone aluminium equivalence) calculated. At each subsequent measurement the RBAE for each horse was compared to its initial RBAE and the percentage change recorded. The mean percentage change is shown in the following table.

| Mean percentage change in RBAE over time | | | | | |
|---|---|---|---|---|---|
| | days | | | | |
| | 9 Sep. 2008 | 14 Oct. 2008 | 31 Dec. 2008 | 2 Feb. 2009 | 8 May 2009 |
| quinaquanone | 0 | 1.04 | 4.54 | 7.68 | 9.05 |
| control | 0 | 0.35 | 2.82 | 3.97 | 5.02 |

FIG. 1 shows the percentage change in radiographic bone density. With reference to the Figure the increase in bone density over time on the horses on Vitamin K1 (Quinaquanone™) in accordance with the invention was 9.05±0.91% compared with the control 5.02±2.17%. 100 days P=NS. 140 days P<0.05. 200 days P<0.01.

Average serum levels of Vitamin K, carboxylated osteocalcin and uncarboxylated osteocalcin were determined as shown in the following table.

| | Average serum levels VitK Ng/mL Sep08 | Average serum % carboxylated osteocalcin Sep08 | Average serum % uncarboxylated osteocalcin Sep08 | Average serum levels VitK Ng/mL May09 | Average serum % carboxylated osteocalcin May09 | Average serum % uncarboxylated osteocalcin Sep08 |
|---|---|---|---|---|---|---|
| No Vit K | 9 ± 10 | 60 ± 7 | 35 ± 7 | 10 ± 9 | 65 ± 9 | 30 ± 7 |
| Vit K | 10 ± 11 | 62 ± 5 | 38 ± 5 | 45 ± 14 | 86 ± 8 | 8 ± 6 |

It can be seen from the Table and FIG. 1 that Vitamin K levels and carboxylated osteocalcin were significantly improved and uncarboxylated osterocalcin significantly reduced in the treated group.

EXAMPLE 11

23 Kg of the above preblend (Example 9) was mixed with 745 gm of vitamin D3 (500,000 IU/gm WS)
5Kg soluble Silica
50 gm boron
and made up to 464 Kg of icing sugar.

EXAMPLE 12

Stable Diluted K1 or K2 Powder in Vitamin Mineral Preblend

10 Kg Vitamin K1 and/or K2 preblend concentrate (example 9)
324 gm Vitamin D3 (500,000 IU/gm WS)
600 Kg Vitamin mineral preblend mixed with high protein concentrate (66% protein) or a combination of wheat pollard, rice pollard, soybean meal, canola meal, cotton seed meal, barley, corn oats and lupins in any combination to maintain the dietary requirements for animals in protein, fat, carbohydrate, vitamins and minerals.

EXAMPLE 13

The formulation of Example 12 can be extruded as a complete feed for animals.

EXAMPLE 14

The available vitamin K levels for various compositions were determined as shown in the following table. This was a human study comparing plasma vitamin K levels (ng/mL) after consuming green vegetation, a vitamin K oil and vitamin K water soluble in accordance with the present invention:

| Source of VK | VK1 serum ng/ml | Bioavailability compared to water soluble vitamin K | Number |
| --- | --- | --- | --- |
| Boiled spinach in milk 500 μg | 2.7 | 12% | 3 |
| Freeze dried spinach in milk 500 μg | 4.7 | 26.4% | 3 |
| VK1 oil in milk 500 μg | 8.24 | 45.6% | 3 |
| Water soluble VK1 in milk 500 μg in accordance with the present invention | 15.11 | 100% | 3 |

This table shows the oral bioavailability of vitamin K in various matrixes after ingestion of a standardised 500 μg amount. The table shows that vitamin K is poorly bioavailable in spinach and in oil compared with water soluble vitamin K in accordance with the present invention.

EXAMPLE 15

It is known that Vitamin K1 (K1) is rapidly degraded by sunlight (UV). For vitamin K1 to be a stable component of a vitamin product, it is necessary to protect it using physical and/or chemical means. It was shown that a loss of approximately 20% of K1 occurred after 4 hours exposure to bright sunlight. Experiments were conducted to determine:

1. If the loss can be reduced by storing paste made in accordance with the present invention without beta carotene in black syringes.
2. If the loss can be reduced by adding beta-carotene to the composition.
3. The effect of encapsulation of Vitamin K1 in a matrix such as cyclodextrin, starch and/or zeolites and the effect of a diluent being a mixture of monosaccharide or disaccharide and starch.

1) Comparison of loss of vitamin K1 from paste stored in a black syringe with that from a white syringe upon UV exposure for 8 hours was conducted. Approximately 5 g of K1 paste as in Example 5 without Beta carotene was taken from each of a 60 mL white syringe and 60 mL black syringe. Each 5 g sample was homogenised and a 1 g sample was taken. The samples were analysed for vitamin K1. The syringes were both placed in direct sunlight for 4 hours after which a second sample of 5 g was taken. The samples were processed as above and assayed for vitamin K1. The syringes were exposed to sunlight for a further 4 hours and the samples again analysed for vitamin K1 as above.

The results are shown in the following table:

| | Vitamin K1 level 0 hours UV exposure | Vitamin K1 level 4 hours UV exposure (Loss) | Vitamin K1 level 8 hours UV exposure (loss) |
| --- | --- | --- | --- |
| White/clear syringe | 1.65 mg/g | 0.99 mg/g (40%) | 0.50 mg/g (70%) |
| Black syringe | 1.65 mg/g | 1.25 mg/g (25%) | 0.92 mg/g (44%) |

It can be seen from this table that the loss of vitamin K1 was more rapid from the paste in the white HDPE (high density polyethylene) container, however the loss of vitamin K1 from the black syringe was too great for the product to be considered UV stable. The results do however show that it is preferable to package the composition in a dark syringe.

2) The effect of the addition of beta-carotene (in accordance with the present invention) on vitamin K1 stability to UV was then determined. It is thought that beta-carotene will protect the vitamin K1, in a paste, exposed to UV light as it will be preferentially photo-oxidised. A water soluble paste containing beta-carotene was prepared according to the following composition as in Example 5.

| PASTE COMPOSITION | |
| --- | --- |
| 35 gm | Vitamin K1 and/or K2 |
| 9.4 Kg | Propylene glycol |
| 9.4 Kg | potable water |
| 105 gm | Polyethoxylated castor oil (PEG35) or TWEEN 80 |
| 35 gm | beta carotene WS10% |
| 800 gm | Vitamin D3 (500,000 iu/gm) WS |
| 100 gm | methyl paraben |
| 660 gm | Xanthan Gum. |

The paste was placed into white (HDPE) 30 mL syringes and treated as follows:

Sample 1—stored at 4° C. for 24 hrs
Sample 2—stored in sunlight for 4 hrs

The results are shown in the following table:

| Sample | Vitamin K1 concentration | % loss |
| --- | --- | --- |
| 1 | 1.7 mg/g | 0 |
| 2 | 1.7 mg/g | 0 |

No loss of vitamin K1 was evident after 4 hrs exposure to sunlight when beta-carotene was included in the composition. This shows that beta-carotene may afford vitamin K1 protection against photo-oxidation.

3). Encapsulation of Vitamin K1 in a powder in accordance with Example 8 using a matrix such as cyclodextrin, starch and/or zeolites and/or as in Example 10, use of a diluent being a mixture of monosaccharide or disaccharide and starch were prepared.

Samples were compared for stability after exposure to 4 hr UV sunlight. Samples were placed in both white HDPE and black HDPE buckets with lids. All samples were made up to 7 mg/10 gm powder before exposure to UV. The results are shown in the following table.

| VITAMIN K POWDER | BLACK bucket HDPE | WHITE bucket HDPE |
|---|---|---|
| Starch | 7 mg K1/10 gm powder (0% loss) | 7 mg K1/10 gm powder (0% loss) |
| Zeolite powder | 7 mg K1/10 gm powder (0% loss) | 7 mg/10 gm powder (0% loss) |
| Cyclodextrin powder | 7 mg K1/10 gm powder (0% loss) | 7 mg K1/10 gm powder (0% loss) |
| Icing sugar/ starch mix | 7 mg K1/10 gm powder (0% loss) | 7 mg K1/10 gm powder (0% loss) |

This example shows that encapsulation of K1 (in accordance with the invention) and use of a diluent being a sugar/starch mix improves its stability.

The foregoing description of preferred embodiments and best mode of the invention known to the applicant at the time of filing the application have been presented for the purposes of illustration and description. It is not intended to be exhaustive or to limit the is invention to the precise form disclosed. Many modifications and variations are possible in the light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

The invention claimed is:

1. A method of increasing bone density, maintaining bone density and/or inhibiting loss of bone density in an equine or avian, comprising:
    administering an effective amount of a water soluble UV stable composition containing:
    vitamin K1, vitamin K2 or a mixture of vitamin K1 and vitamin K2, together with a physiologically acceptable carrier, excipient and/or diluent, wherein the vitamin K1 and/or vitamin K2 is emulsified together with a UV absorber or is encapsulated into a modified starch or cyclodextrin to an equine or avian diagnosed with or at risk of bone loss,
    wherein said administering increases bone density, maintains bone density, or inhibits loss of bone density in said equine or avian.

2. A method according to claim 1, wherein the composition is administered orally.

3. A method according to claim 1, comprising:
    administering a water soluble UV stable composition containing vitamin K1, vitamin K2 or a mixture of vitamin K1 and vitamin K2, a UV absorber and a physiologically acceptable carrier, excipient and/or diluent and with or without an adjunct vitamin or mineral, to reach about the maximum achievable level of carboxylated osteocalcin in the equine or avian being treated.

4. A method according to claim 3, wherein the composition is administered orally.

* * * * *